United States Patent
Migliaccio et al.

(10) Patent No.: US 10,350,179 B2
(45) Date of Patent: Jul. 16, 2019

(54) COMBINATION COMPRISING PALMITOYLETHANOLAMIDE (PEA) AND LYCOPENE FOR USE IN THE TREATMENT OF INFLAMMATORY DISEASES

(71) Applicant: Raffaele MIGLIACCIO, Monza (IT)

(72) Inventors: Raffaele Migliaccio, Monza (IT); Antonella Sardei, Molina di Malo (IT); Carmela Migliaccio, Monza (IT)

(73) Assignee: Raffaele MIGLIACCIO, Monza (IT)

( * ) Notice: Subject to any disclaimer, the term of this patent is extended or adjusted under 35 U.S.C. 154(b) by 0 days.

(21) Appl. No.: 15/577,439

(22) PCT Filed: May 31, 2016

(86) PCT No.: PCT/IB2016/053191
§ 371 (c)(1),
(2) Date: Nov. 28, 2017

(87) PCT Pub. No.: WO2016/193905
PCT Pub. Date: Dec. 8, 2016

(65) Prior Publication Data
US 2018/0140565 A1    May 24, 2018

(30) Foreign Application Priority Data
Jun. 4, 2015   (IT) .................. 102015000020469

(51) Int. Cl.
*A61K 31/164*   (2006.01)
*A61K 31/01*    (2006.01)
*A61P 29/00*    (2006.01)

(52) U.S. Cl.
CPC ............ *A61K 31/164* (2013.01); *A61K 31/01* (2013.01); *A61P 29/00* (2018.01); *A61K 2300/00* (2013.01)

(58) Field of Classification Search
None
See application file for complete search history.

(56) References Cited

U.S. PATENT DOCUMENTS

2013/0172407 A1* 7/2013 Kuo .................. A61K 31/01
514/475

FOREIGN PATENT DOCUMENTS

| EP | 0570714 | 11/1993 |
|---|---|---|
| NL | 2011448 | 1/2015 |
| WO | WO 2009/007975 A1 | 1/2009 |

OTHER PUBLICATIONS

Bachur, et al., The Journal of Biological Chemistry, vol. 240, No. 3, p. 1019-1024.
Hansen, et al., Chemistry and Physics of Lipids, vol. 108, p. 135-150, Mar. 10, 2000.
Hansen, et al., Experimental Neurology, vol. 224, No. 1, p. 48-55, Jul. 1, 2010.
International Search Report for PCT/IB2016/053191 dated Sep. 19, 2016.
Italian Search Report With Written Opinion for IT102015000020469 dated Jan. 19, 2016.
Lin Hsiao-Yun, et al., Neurobiology of Aging, vol. 35, No. 1, p. 191-202, Jul. 30, 2013.
Pertwee, et al., Pharmacological Reviews, vol. 62, No. 4, p. 588-631, 2010.
Pfannkuch, et al., Handbook of Pharmaceutical Salts Properties, Selection and Use, Forward & Chapter 5, pp. 116 and 125-133, 2008.
Sachdeva Anand Kamal, et al., Journal of Nutritional Biochemistry, vol. 26, No. 7, p. 736-744, Mar. 20, 2015.
Schäbitz, et al., Journal of the American Heart Association, Stroke, vol. 33, p. 2112-2114, 2002.
Gaetani, et al., J. Neurochem., 2016, 139, 691-699.
Ho, et al., British Journal of Pharmacology, 2008, 155, 837-846.

* cited by examiner

*Primary Examiner* — Yong L Chu
(74) *Attorney, Agent, or Firm* — Hueschen and Sage

(57) ABSTRACT

The object of the present invention is the combination of palmitoylethanolamide (PEA) and lycopene, and/or pharmaceutically acceptable salts and/or derivatives thereof, the pharmaceutical formulations comprising the combination of PEA and lycopene, and/or pharmaceutically acceptable salts or derivatives thereof, optionally together with at least one pharmacologically acceptable excipient, and the use of the combination of PEA and lycopene, and/or pharmaceutically acceptable salts or derivatives thereof, and of the formulations comprising such a combination, in the treatment of inflammatory diseases.

16 Claims, No Drawings

COMBINATION COMPRISING PALMITOYLETHANOLAMIDE (PEA) AND LYCOPENE FOR USE IN THE TREATMENT OF INFLAMMATORY DISEASES

The object of the present invention is the combination of palmitoylethanolamide (PEA) and lycopene, and/or pharmaceutically acceptable salts and/or derivatives thereof, the pharmaceutical formulations comprising the combination of PEA and lycopene, and/or pharmaceutically acceptable salts and/or derivatives thereof, optionally together with at least one pharmacologically acceptable excipient, and the use of the combination of PEA and lycopene, and/or pharmaceutically acceptable salts and/or derivatives thereof, and of the formulations comprising such a combination, in the treatment of inflammatory diseases.

STATE OF THE ART

The inflammatory response is a multifactorial physiological reaction characterized by the participation of different cells of the immune system, such as, for example, mastocytes, macrophages, basophils and/or lymphocytes having different timing of intervention.

The first cell to intervene in the inflammatory process is the mastocyte, whose response capacity to trigger the inflammatory process is in the order of microseconds. Its activation generates a series of reactions following the release of preformed mediators contained inside its cytoplasm; in rapid succession the recall and then the activation of macrophages take place.

The biological systems are based on receptor control: following the stimulation of the pathogenic agent, the cells express specific receptors that are saturated by self-produced mediators, i.e. mediators that are formed by fatty acids constituting the membranes of the same cells. The expression of receptors is the system through which the cells that are involved in the inflammatory process succeed in "transferring" growth factors, interleukins, cytokines, etc., to the microenvironment. The saturation of such receptors first enables to reduce, and subsequently to modulate the degranulation of mediators that are present inside the cytoplasm of the cells involved in the inflammatory process, which are mainly mastocytes, until the stimulus induced by the presence of the pathogenic agent is stopped.

However, this regulatory system is exhausted at the time when the continuing depletion of the cellular membranes of fatty acids causes the cell to suffer. In this condition, the receptors remain overexpressed, and for the cell this is a signal for degranulation of those mediators that trigger defense phenomena that are no longer necessary.

It is thus clear that, should receptor control not occur, the cells would degranulate everything found in the cytoplasm with the resulting recall of other cells in the microenvironment, and this would exasperate the system that, by remaining active, could become a source of harm, and give rise to chronic and autoimmune inflammatory diseases such as, for example, rheumatoid arthritis, multiple sclerosis, and systemic lupus erythematosus.

In these pathological conditions, it is therefore very important for the organism to be able to control the hyperactivation of the inflammatory process through the formation of the receptor antagonist consisting of fatty acids removed from the membrane of the same cells.

Until today, in order to respond to this need, dietary strategies have been devised to reduce the synthesis of pro-inflammatory chemical mediators, such as prostaglandins, through the reduction of the consumption of vegetable oils and fatty meats, and the promotion of the consumption of fish and certain peculiar oils, such as linseed oil and hemp seed oil. By doing so, it was assumed that greater quantities of eicosapentaenoic acid and docosahexaenoic acid (omega-3) would be incorporated by the membrane phospholipids in place of arachidonic acid.

It is nevertheless known that these dietary strategies are not sufficient to eradicate important inflammatory diseases, such as, for example, rheumatoid arthritis, chronic ulcerous colitis, systemic lupus erythematosus, pelvic inflammatory disease, or also atherosclerosis, and it is therefore necessary to resort to pharmacological treatments. The pharmacological treatments currently used for inflammatory diseases are corticosteroids (such as, for example, cortisone and the like) or NSAIDS (nonsteroidal anti-inflammatory drugs), which are drugs that act at different levels of the arachidonic acid cascade.

The function of this cascade is to trigger the immune response, to sustain it until the danger is eliminated, and then to dampen the immune response so that it doesn't become harmful (as it does occur, for example, in chronic inflammations or in autoimmune diseases). In particular, corticosteroids inhibit the cellular processes leading to the synthesis of proinflammatory and immunostimulant substances, and, vice versa, activate those cellular processes leading to the synthesis of anti-inflammatory and immunosuppressive substances, so as to reduce the symptoms of the disease.

The side effects of synthetic corticosteroids mostly depend on the fact that, in addition to the anti-inflammatory/immunosuppressive effect, they interfere with the organism's homeostatic systems, and thus may cause: hypertension, water retention, hyperglycemia, potassium loss, osteoporosis, muscular hypertrophy, capillary fragility, delayed wound healing, hyperlipidemia, accumulation of adipose tissue in the face, neck and abdomen, gastroduodenal ulcers, increased blood clotting, hematological changes, euphoria and insomnia.

With prolonged treatment, these drugs tend to inhibit the production of similar natural hormones by the adrenal glands, thus causing adrenal insufficiency, which manifests itself with possibly serious consequences, especially when the treatment is suspended. Moreover, the protracted use of corticosteroids is linked to their immunosuppressive action, that increases susceptibility to infection.

NSAIDS, by contrast, interfere at a different level with the arachidonic acid cascade, inhibiting the COX1 and 2 cyclooxygenase involved in the inflammatory processes. Among side effects, the most common ones affect the gastroenteric apparatus, and in particular the stomach: with pain, or burning, or nausea, ulceration of the gastric mucosa, with possible bleeding; skin reactions (rashes, urticaria) in predisposed subjects.

It is therefore felt the need to identify one or more compounds for treating inflammation that are able to effectively block hyperactivation of the inflammatory process, reducing the side effects associated with traditional treatments.

One of the further consequences of the inflammatory process is the production of free radicals, as a factor resulting from reactions aimed at counteracting the pathogenic agent, and more in general to cope with the reactions induced by any pathological damage. The release of free radicals results to be a further stimulating factor to cells involved in the process of counteracting the pathological damage. The presence of free radicals is, therefore, a further inflammatory, of sustainment and amplification factor of the process itself.

It is therefore extremely important to be able to effectively counteract the activity of free radicals in order to counteract an additional inflammatory stimulation factor.

It has now surprisingly been found that a combination comprising palmitoylethanolamide (PEA) and lycopene is able to efficiently treat the inflammatory process, with an improved control of the regulatory system, and in the absence of side effects, through the biological control of the cells involved in the inflammatory process.

Palmitoylethanolamide is an endogenous compound, belonging to the class of fatty acids amides, and it is chemically known as N-(2-hydroxyethyl)hexadecanamide. This compound is a key element in the regulation of pathways linked to the inflammation process, in particular in the down-regulation of the mastocytes degranulation process, and also of processes underlying itching and pain.

Data on the physiological presence of palmitoylethanolamide in different organs of mammals are reported in many publications; in humans, this particular lipid is present in many organs and particularly in the central and peripheral nervous system, skin, spleen, plasma (Bachur N R et al., J. Biol Chem, 1965; 240(3): 1019-1024.) (Hansen H S. Et al., Chem and Phys. of Lipids. 2000; 108:135-150).

In the organism, the physiological levels of palmitoylethanolamide are regulated as a function of different cell stress (H S Hansen. Exp Neurol. 2010; 224 (1): 48-55); moreover, in pathological conditions involving cellular suffering and a resulting state of tissue hyper-reactivity, significant variations in endogenous levels of palmitoylethanolamide were highlighted (Schäbitz W R et al., Stroke. 2002; 33(8):2112-4).

The biological significance of the presence of palmitoylethanolamide, and its function in the organism, is characterized in that this lipid having an N-acylethanolamide structure physiologically intervenes to maintain tissue reactivity within limits compatible with the homeodynamic equilibrium of the district.

Data in the literature have shown that the endogenously synthesized palmitoylethanolamide has the function of ensuring the necessary nerve tissue neuroprotection, and neurodegeneration control (Hansen H S. Exp Neurol. 2010; 224(1):48-55).

The molecular mechanism by which the endogenous palmitoylethanolamide exerts its inhibitory effect on neuroinflammation is that of inhibitory control, of antagonist type, on non-neuronal cells, both mastocytes and microglia, which are activated in response to exogenous and/or endogenous supramaximal excitatory stimuli; particularly on the mastocytes residing in both peripheral and central tissues, and in spinal and supraspinal microglia.

Lycopene is a non-polar alkyl compound composed of only hydrogen and carbon, belonging to the carotenoid group. It is a food additive used as a dye, and identified by the initials E160d.

The major dietary source of lycopene is represented by the tomato (*Solanum lycopersicum*), from which it is named, and its derivatives, in which it represents 60% of the total carotenoid content. Other natural sources of lycopene are melon, guava, and pink grapefruit. The concentration of lycopene in human serum is closely related to the prolonged intake of these raw materials, mainly in heat-treated products (e.g. tomato sauce) compared to raw products. Lycopene is the predominant carotenoid in human plasma, where its concentrations range from 0.22 to 1.06 nmol/mL. Since lycopene is a lipophilic substance, its absorption is related to the presence of fats in the diet. In the intestine, in the presence of bile acids, lycopene is solubilized, incorporated in micelles, and absorbed by the mucous membrane by passive transport. The intact molecule may be incorporated into chylomicrons and transported inside the lymphatic system. It appears that there are no specific transport proteins for this compound, but it is transported by lipoproteins, especially low-density ones (LDL).

There is currently little known about the hepatic metabolism of lycopene; however, like the other carotenoids, lycopene is incorporated into chylomicrons and it is released into the lymphatic system. In the plasma, lycopene is transported by very low density lipoproteins (VLDL) and by low density lipoproteins (LDL). Lycopene is present at higher concentrations in adipose tissue, adrenal glands, liver and testis. Although lycopene does not have activity as a vitamin A precursor, it is an exceptional antioxidant, by virtue of its alkyl structure, the number of conjugated double bonds, and its high hydrophobicity. In general, carotenoids are powerful antioxidants, thanks to their effectiveness as "scavengers" of free radicals. Among the carotenoids, lycopene seems to be the most efficient "oxygen quencher", capable of capturing the free radicals, due to the presence of two additional double bonds with respect to the structure of other carotenoids.

Lycopene, like other carotenoids, is active in the prevention of cancer; several published studies attributed to lycopene the ability to reduce the risk of prostate cancer in humans, and experimental studies on mice suggest that it has the ability to suppress the growth of breast cancer cells. The anticancer action of lycopene was also observed at gastrointestinal, endometrial, and skin level.

Definitions

Unless otherwise defined, all terms of the art, notations and other scientific terms used herein are intended to have the meanings commonly understood by those skilled in the art to which this description belongs. In some cases, terms with meanings that are commonly understood are defined herein for clarity and/or ready reference; therefore, the inclusion of such definitions herein should not be interpreted as being representative of a substantial difference with respect to what is generally understood in the art.

The term "pharmaceutically acceptable excipient" refers to a substance devoid of any pharmacological effect of its own, and that does not produce adverse reactions when administered to a mammal, preferably a human being. Pharmaceutically acceptable excipients are well known in the art and are described, for example, in *Handbook of Pharmaceutical Excipients, sixth edition* 2009, incorporated herein by reference.

The excipients are generally classified according to their function in the final pharmaceutical composition. Preferably, excipients suitable according to the present invention are, for example, diluents, absorbents, glidants, binders, lubricants, surfactants, disintegrants, preservatives, antioxidants, or mixtures thereof.

The term "pharmaceutically acceptable salts or derivatives" refers to those salts or derivatives which possess the biological effectiveness and properties of the salified or derivatized compound, and that do not produce adverse reactions when administered to a mammal, preferably a human being. The pharmaceutically acceptable salts may be inorganic or organic salts; examples of pharmaceutically acceptable salts include, but are not limited to: carbonate, hydrochloride, hydrobromide, sulfate, hydrogen sulfate, citrate, maleate, fumarate, trifluoroacetate, 2-naphthalenesulfonate, and para-toluenesulfonate. Additional information on pharmaceutically acceptable salts may be found in *Handbook of pharmaceutical salts*, P. Stahl, C. Wermuth, WILEY-VCH, 127-133, 2008, incorporated herein by reference. The pharmaceutically acceptable derivatives include esters, ethers and N-oxides.

The term "simultaneous, separate or sequential use" refers to the simultaneous administration of the first and the second compound, or in such a way that the two compounds will act in the body of the patient at the same time, or to the administration of a compound after the other compound in such a way to provide a therapeutic effect. In some embodiments, the compounds are taken with a meal. In other embodiments, the compounds are taken after a meal, such as 30 minutes, or 60 minutes after a meal. In some embodiments, a compound is administered to a patient for a period of time, followed by the administration of the other compound.

The terms "comprising", "having", "including", and "containing" are to be intended as open terms (i.e., meaning "comprising, but not limited to"), and are to be considered as a support also for terms such as "consist essentially of", "consisting essentially of", "consist of", or "consisting of".

DESCRIPTION OF THE INVENTION

It has surprisingly been found that a combination comprising palmitoylethanolamide (PEA) and lycopene is able to efficiently treat the inflammatory process, with an improved control of the regulatory system, and in the absence of side effects, through the biological control of the cells involved in the inflammatory process.

In particular, by means of the association between PEA and lycopene according to the present invention, it is possible to obtain the control of the cells involved in inflammatory processes, such as mastocytes, macrophages, basophils, and lymphocytes, and, at the same time, counteract the inflammatory stimulation activity determined by the presence of free radicals as consequences of the same process. It has, in fact, been observed that the combination of PEA, and lycopene and/or pharmaceutically acceptable salts and/or derivatives thereof, is able to efficiently treat inflammatory diseases.

An object of the present invention is therefore a combination comprising PEA and lycopene, and/or pharmaceutically acceptable salts and/or derivatives thereof. According to a preferred aspect, the percentage amount of PEA, and/or pharmaceutically acceptable salts and/or derivatives thereof, is comprised between 0.5% and 99.5% of the combination, and the percentage amount of lycopene, and/or pharmaceutically acceptable salts and/or derivatives thereof, is comprised between 0.5% and 99.5% of the combination, wherein said percentages are based on the total weight of the combination.

Particularly preferred are the combinations comprising PEA, and lycopene, and/or pharmaceutically acceptable salts and/or derivatives thereof, wherein the percentage amount of PEA and lycopene in the combination are, respectively: 90% and 10%, or 80% and 20%, or 70% and 30%, or 60% and 40%, wherein said percentages are based on the total weight of the combination.

A further object of the present invention is represented by the combination comprising PEA and lycopene, and/or pharmaceutically acceptable salts and/or derivatives thereof, for use in the treatment of inflammatory diseases.

Preferred diseases, according to the present invention, are inflammatory diseases related to hyperactivity of the cells involved in the inflammatory processes, also as a result of oncogenic phenomena, more preferably neuro-inflammatory diseases of the peripheral and central nervous system.

Said inflammatory diseases may be acute or chronic, and are preferably selected from dermatological diseases, ophthalmic diseases, mucosal diseases, joint and/or connective tissue diseases, chronic pathological inflammation, degenerative diseases of the peripheral nervous system (PNS) and central nervous system (CNS), cardiologic diseases deriving from perfusion phenomena as a consequence of ischemic damage, inflammatory diseases associated with fibrosis, wound healing abnormalities, or diseases in which the renal function is impaired as a result of kidney inflammation.

Preferably, said dermatological diseases are selected from atopic dermatitis, dermatomyositis, scleroderma, psoriasis, polymyositis, pemphigus, or bullous pemphigoid epidermolysis.

Preferably, said ophthalmic diseases are selected from Sjogren's syndrome, sympathetic ophthalmia, uveitis, uveoretinitis, macular degeneration, or glaucoma.

Preferably, said mucosal diseases are selected from inflammation of the gastrointestinal mucosal membranes (Crohn's disease), or inflammation of the mucous membranes of the mouth and genitals.

Preferably, said joint and connective tissue diseases are selected from rheumatoid arthritis, psoriatic arthritis, lupus erythematosus arthritis, or systemic and discoid lupus erythematosus.

Preferably, said chronic pathological inflammation are selected from chronic solar dermatitis, asthma, and intestinal and pulmonary fibrosis, or chronic arthritis.

Preferably, said degenerative diseases of the peripheral nervous system (PNS) and central nervous system (CNS) are selected from multiple sclerosis, neurodegenerative disorders not only autoimmune, inflammatory processes associated with CNS, such as Parkinson's disease, gambling, senile dementia, tinnitus, bacterial meningitis, HIV infections, and traumatic injuries, PNS diseases such as, for example, radiculopathy caused by inflammation; peripheral and central nervous system diseases wherein inflammation processes follow the first insult of ischemic origin, such as, for example, neuropathies due to compression and trauma, brain stroke, traumatic brain injury, tinnitus, polyneuropathy, myasthenia, myopathy, or peripheral neuropathies due to etiologies such as that induced by chemotherapy in oncologic patients.

Preferably, said cardiologic diseases resulting from perfusion phenomena as a consequence of ischemic damage are selected from stroke, ischemic heart disease, coronary angioplasty, or coronary artery bypass.

Preferably, said inflammatory diseases associated with fibrosis are selected from allergic conjunctivitis, giant papillary conjunctivitis, or dietary allergies.

Preferably, said wound healing abnormalities are selected from hypertrophic scars, keloid scars, or ocular pemphigoid.

Preferably, said diseases in which renal function is impaired as a result of kidney inflammation are selected from peripheral neuropathies, impaired glomerular filtration (creatininemia), nephritis, or glomerulonephritis.

The use of the combination is intended also for veterinary use in the animal diseases corresponding to the human ones indicated above.

Without being bound to any particular theory, it is believed that the synergistic effect of the combination comprising PEA and lycopene, and/or pharmaceutically acceptable salts and/or derivatives thereof, is due to the regulating activity of PEA on the inflammatory process, and also to the regulating activity of lycopene on the immune system cells in the course of processes of hyperactivation of immune system cells, as it occurs in the course of inflammatory processes, in addition to the capacity of recovery of physiological conditions in a short time, and the normal conditions of the microenvironment involved, with respect to what It is known in the art.

Although the regulatory activity of PEA on the inflammatory process and the regulatory activity of lycopene on the immune system cells were known, the combination of lycopene and PEA of the present invention has surprisingly shown a significant synergistic effect on the treatment of inflammation, compared to the effect of the individual components.

In particular, the combination comprising PEA and lycopene, and/or pharmaceutically acceptable salts and/or derivatives thereof, is for simultaneous, separate or sequential use in the prevention and/or treatment of the diseases indicated above. That is, the active ingredients of the inventive combination may be administered simultaneously, separately, or sequentially.

According to preferred embodiments of the present invention, the combinations are administered by oral, topical, otological, ophthalmic, rectal, vaginal, or parenteral route.

Preferably, when the administration of the combinations of the invention is performed by oral route, the pharmaceutical form is selected from tablet, capsule, granule, powder, oily pearl, solution, suspension, aerosol, and still more preferably said oral form is selected from tablet, capsule, granule, or solution.

Preferably, when the administration of the combinations of the invention is performed by topical route, the pharmaceutical form is selected from cream, ointment, gel, salve, solution, washing, suspension, drops, buffer (buffer solution), suspension, eye drops, drops, spray, wipe, or powder, and it is preferably selected from cream, gel, spray, or ointment.

Among the topical administration routes, the topical administration by otological route, and in this case the pharmaceutical form is preferably selected from washing, spray, drops, cream or buffer, and the ophthalmic administration, and in this case the pharmaceutical form is preferably selected from eye drops, wash, wipe, spray or cream, may also be comprised.

Preferably, when the administration of the combinations of the invention is performed by rectal route, the pharmaceutical form is selected from cream, suppository, or enema.

Preferably, when the administration of the combinations of the invention is performed by vaginal route, the pharmaceutical form is selected from cream, ovule, wipe, or cannula.

Preferably, when the administration of the combinations of the invention is performed parenterally, the pharmaceutical form is selected from buffer aqueous solution or oily suspension, and still more preferably said parenteral form is an oily suspension.

A further object of the present invention is a composition comprising the combination of PEA and lycopene, and/or pharmaceutically acceptable salts and/or derivatives thereof, optionally together with at least one pharmacologically acceptable excipient. In a preferred aspect, the composition of the present invention contains from 0.5% to 99.5% of the PEA and lycopene combination, preferably from 40% to 70%, wherein said percentages are based on the total weight of the composition.

The compositions comprising the combination of PEA and lycopene, and/or pharmaceutically acceptable salts and/or derivatives thereof, together with at least one pharmacologically acceptable excipient, are suitable for use in the treatment of the diseases indicated above for the combination of PEA and lycopene, and/or pharmaceutically acceptable salts or derivatives thereof. Preferably, said compositions are for simultaneous, separate or sequential use in the prevention and/or treatment of all the diseases indicated above.

According to preferred embodiments of the present invention, the compositions comprising the combination of the present invention together with a pharmaceutically acceptable excipient are compositions administrable by oral, topical, otological, ophthalmic, rectal, vaginal or parenteral route.

Preferably, when the administration of the compositions of the invention is performed by oral route, the pharmaceutical form is selected from tablet, capsule, granule, powder, oily pearl, solution, suspension, or aerosol, and still more preferably said oral form is selected from tablet, capsule, granule, or solution.

Preferably, when the administration of the compositions of the invention is performed by topical route, the pharmaceutical form is selected from cream, ointment, gel, salve, solution, washing, suspension, drops, buffer (buffer solution), suspension, eye drops, drops, spray, wipe, or powder, preferably it is selected from cream, gel, spray, or ointment.

Among the topical administration routes, the topical administration by otological route, and in this case the pharmaceutical form is preferably selected from washing, spray, drops, cream or buffer, and the ophthalmic administration, and in this case the pharmaceutical form is preferably selected from eye drops, wash, wipe, spray or cream, may also be comprised.

Preferably, when the administration of the compositions of the invention is performed by rectal route, the pharmaceutical form is selected from cream, suppository, or enema.

Preferably, when the administration of the compositions of the invention is performed by vaginal route, the pharmaceutical form is selected from cream, ovule, wipe, or cannula.

Preferably, when the administration of the compositions of the invention is performed parenterally, the pharmaceutical form is selected from buffer aqueous solution or oily suspension, and still more preferably said parenteral form is an oily suspension. According to a preferred embodiment of the present invention, the formulations comprising the combination of PEA and lycopene, and/or pharmaceutically acceptable salts and/or derivatives thereof, together with at least one pharmacologically acceptable excipient, are administered daily, preferably one or more times per day.

According to a preferred aspect, the daily administration contemplate from one to four doses per day, preferably two or four daily doses, wherein said doses preferably contain from 0.1 to 50 mg of the combination of the invention per kg of patient body weight, preferably from 0.5 to 20 mg per kg of patient body weight.

According to a further preferred aspect of the invention, daily administration is continued for a period of at least 15 days, preferably of at least 30 days, still more preferably of at least 90 days. According to a further preferred aspect, such a daily administration is continued for at least 30 days or for at least 60 days.

According to a further preferred embodiment of the present invention, the composition of the invention is administered orally, preferably in the form of tablets, beads or capsules, two or four times a day, for a period of at least 15 days, preferably of at least 30 days, still more preferably of at least 90 days. According to a further preferred aspect, such a daily administration is continued for at least 30 days or for at least 60 days.

According to a further preferred aspect, each of the tablets indicated above comprise from 100 to 700 mg of PEA and from 0.5 to 60 mg of lycopene, and even more preferably comprise 300, 400, or 600 mg of PEA and 5, 15, or 30 mg of lycopene. Still more preferably, the tablets indicated above contain 300 mg of PEA and 15 mg of lycopene, or contain 400 mg of PEA and 25 mg of lycopene, or contain 600 mg of PEA and 30 mg of lycopene, or 400 mg of PEA and 20 mg of lycopene.

In a further object, the composition of the present invention may be administered to animals and to humans, intended both as adult subject and "pediatric population", wherein the term "pediatric population" identifies that part of the population aged between birth and eighteen years.

EXAMPLES

The following formulations according to the present invention were prepared.

Example 1. Cream Formulation

| Lycopene | 10% |
|---|---|
| Palmitoylethanolamide | 30% |
| Hyaluronic acid | 1% |
| Tocopherol | 2% |
| Palmitic acid | 3% |
| Excipients | 54% |

Example 2: Drops Formulation

| Lycopene | 1% |
|---|---|
| Palmitoylethanolamide | 50% |
| Vitamin C | 10% |
| Excipients | 39% |

Example 3: Suspension Formulation

| Lycopene | 2% |
|---|---|
| Palmitoylethanolamide | 48% |

-continued

| Vitamin D | 5% |
|---|---|
| Vitamin C | 3% |
| Excipients | 42% |

Example 4: Tablet Formulation

| Lycopene | 20% |
|---|---|
| Palmitoylethanolamide | 40% |
| Pyroglutamic acid | 10% |
| Excipients | 30% |

Example 5. Powder/Granules Formulation

| Lycopene | 30% |
|---|---|
| Palmitoylethanolamide | 70% |

Example 6

Assessment of the effect of a composition comprising PEA (350 mg) and lycopene (5 mg), in patients with glaucoma.

In the study described six patients were evaluated.

Inclusion Criteria:
Age not less than 50 years;
Age not over 75 years;
Presence of comorbidities;
Ocular pressure increase≥21 mmHg
Positive eye examination.
Patient perception of visual acuity loss confirmed by specialist visit
Patients characteristics are included in Table 1

TABLE 1

| Patient | Sex | Age | Other Primary Disease | Smoking | IOP mmHg | Visual Acuity Reduction | Need of More Light | Difficulty in Facial Recognition |
|---|---|---|---|---|---|---|---|---|
| F.T. | F | 56 | HYPERTENSION | YES | 21 | YES | YES | YES |
| D.R. | M | 71 | DIABETES | NO | 22 | YES | YES | YES |
| L.C. | M | 68 | DIABETES | NO | 21 | YES | YES | NO |
| G.T. | F | 55 | HYPERTENSION | YES | 23 | YES | YES | YES |
| M.E. | M | 73 | HYPERTENSION | NO | 21 | YES | NO | YES |
| O.F. | F | 69 | DIABETES | NO | 22 | YES | NO | YES |

Patients were asked to continue with the ongoing therapy and to add the new compound.

All patients were given the compound in tablets for six months, at two tablets a day. At the end of the treatment, all patients were subjected to blood tests for the assessment of changes in parameters, and to eye examination with fundus.

Results

At the end of the planned period, none of the patients had discontinued the treatment; none of the patients had experienced product related side effects.

The data at the end of the 180 day treatment are reported in Table 2.

TABLE 2

| Patient | Sex | Age | Other Primary Disease | Smoking | IOP mmHg | Visual Acuity Reduction | Need of More Light | Difficulty in Facial Recognition |
|---|---|---|---|---|---|---|---|---|
| F.T. | F | 56 | HYPERTENSION | YES | 18 | YES | NO | YES |
| D.R. | M | 71 | DIABETES | NO | 19 | NO | NO | NO |
| L.C. | M | 68 | DIABETES | NO | 16 | NO | NO | NO |
| G.T. | F | 55 | HYPERTENSION | YES | 20 | NO | NO | NO |
| M.E. | M | 73 | HYPERTENSION | NO | 19 | NO | NO | YES |
| O.F. | F | 69 | DIABETES | NO | 18 | NO | NO | NO |

Study Analysis

To assess the compound activity, five "symptoms" were assessed, and the global conditions of the symptoms after the treatment were recorded:

Visual acuity reduction: improvement in 30% of the patients

Need of more light: improvement in 76% of the patients

Reduction of the intraocular pressure: improvement in 100% of the patients

Difficulty in facial recognition: improvement in 51% of the patients

In terms of tolerability profile, the compound showed excellent tolerability: no patients abandoned the study, or experienced side effects.

Conclusions

The study shows a more than surprising action in controlling and reducing the intraocular pressure, with an improvement of the "symptoms" attributable to a compression of the ocular nerve. In addition, it shows a significant efficacy in the control and, above all, a marked improvement of the pathological conditions.

The compound used has therefore proved effective in controlling the progression of glaucoma.

Example 7

Assessment of the results of the treatment with a composition comprising PEA and Lycopene on the pain of cancer patients, under chemotherapy, with symptoms of peripheral neuropathy.

Patients assessed: 5 patients, under chemotherapy, with symptoms of neuropathy selected from among the patients under weekly treatment with Paclitaxel.

Inclusion Criteria:

Patients under chemotherapy (Paclitaxel)

Presence of neuropathy with moderate signs and symptoms, based on the scores attributed to MNSI (Michigan Neuropathy Screening Instrument, score>2) and TTS (Total Symptom Score) questionnaires, respectively.

Assessment Parameters:

The presence of signs and symptoms of diabetic neuropathy, and their intensity, will be assessed by the administration of the following questionnaires:

MNSI (Michigan Neuropathy Screening Instrument)

TTS (Total Symptom Score).

NPSI (Neuropatic Pain Symptom inventory)

Composition used: Lycopene 5 mg+PEA 350 mg

Dosage: 2 cpr/day (one every 12 hours) for 30 days.

ASSESSMENT TIMEPOINT: at baseline (T0), at day 15 after initiation of treatment (T1), at day 30 of treatment (T2).

PRIMARY OBJECTIVE: to assess whether the administration of the compound PEA+Lycopene, 350 mg+5 mg, induces a decrease/attenuation of the intensity of signs and symptoms of the peripheral neuropathy assessed by the score attributed to the Questionnaires.

SECONDARY OBJECTIVE: To assess tolerability, safety and patients' compliance.

RESULTS: 5 patients were enrolled within the inclusion criteria. All the patients were subjected to weekly administration of Paclitaxel in the presence of peripheral neuropathy.

At the end of the study all the patients had completed the study.

Conclusions

Preliminary results at the end of the study concerning the 5 patients showed that:

3 patients had no symptoms of peripheral neuropathy 2 patients had significantly decreased symptoms of peripheral neuropathy, and improvement of their quality of life.

The association PEA+Lycopene showed to be able to effectively control the onset of peripheral neuropathy resulting from weekly treatment with Paclitaxel.

At the end of the study, 60% of the patients did not manifest any symptoms of peripheral neuropathy.

40% of the patients had a significant improvement in both symptoms of peripheral neuropathy and quality of life.

Therefore, the association PEA+Lycopene represents a valuable tool for controlling the onset of peripheral neuropathy induced by Paclitaxel, with an excellent tolerability profile.

The invention claimed is:

1. A combination comprising palmitoylethanolamide and lycopene, and/or pharmaceutically acceptable salts thereof, wherein the percentage amount of palmitoylethanolamide is about 70% of the combination, based on the total weight of the combination, and wherein the percentage amount of lycopene is about 30% of the combination, based on the total weight of the combination.

2. A composition comprising the combination according to claim 1, optionally together with at least one pharmacologically acceptable excipient.

3. A method of treating inflammatory diseases in a subject in need thereof, comprising administration of an effective amount of the combination according to claim 1, alone or in combination with at least one pharmacologically acceptable excipient, wherein the inflammatory disease is glaucoma or peripheral neuropathies induced by chemotherapy in oncologic patients.

4. The method according to claim 3, wherein the combination is administered simultaneously, separately, or sequentially.

5. The method according to claim 3, wherein the combination is formulated in an oral, topical, ophthalmic, rectal, vaginal or parenteral form.

6. The method according to claim 5, wherein the combination is formulated in an oral form selected from the group consisting of a tablet, a capsule, a granule, a powder, an oily pearl, a solution, a suspension, and an aerosol.

7. The method according to claim 5, wherein the combination is formulated in a topical form selected from the group consisting of a cream, an ointment, a gel, a salve, a solution, a washing, a suspension, drops, a spray, a wipe, and a powder.

8. The method according to claim 5, wherein the combination is formulated in a parenteral form selected from the group consisting of a buffer aqueous solution and an oily suspension.

9. The method according to claim 3, wherein the combination is administered daily.

10. The method according to claim 9, wherein the combination is administered one to four times per day.

11. The method according to claim 10, wherein the combination is administered two to four times per day at dosage of from 0.1 to 50 mg of the combination per kg of patient body weight.

12. The method according to claim 11, wherein the dosage is from 0.5 to 20 mg of the combination per kg of patient body weight.

13. The composition according to claim 2, wherein the combination is formulated in an oral, topical, ophthalmic, rectal, vaginal or parenteral form.

14. The composition according to claim 13, wherein the combination is formulated in an oral form selected from the group consisting of a tablet, a capsule, a granule, a powder, an oily pearl, a solution, a suspension, and an aerosol.

15. The composition according to claim 13, wherein the combination is formulated in a topical form selected from the group consisting of a cream, an ointment, a gel, a salve, a solution, a washing, a suspension, drops, a spray, a wipe, and a powder.

16. The composition according to claim 13, wherein the combination is formulated in a parenteral form selected from the group consisting of a buffer aqueous solution and an oily suspension.

* * * * *